(12) United States Patent
Niu et al.

(10) Patent No.: US 10,598,660 B2
(45) Date of Patent: Mar. 24, 2020

(54) APPLICATION OF ANAPLASMA PHAGOCYTOPHILUM PROTEIN APH1384

(71) Applicant: SOOCHOW UNIVERSITY, Suzhou (CN)

(72) Inventors: Hua Niu, Suzhou (CN); Meiling He, Suzhou (CN); Shuyan Wu, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 16/321,824

(22) PCT Filed: Jun. 12, 2017

(86) PCT No.: PCT/CN2017/087912
§ 371 (c)(1),
(2) Date: Jan. 29, 2019

(87) PCT Pub. No.: WO2018/166079
PCT Pub. Date: Sep. 20, 2018

(65) Prior Publication Data
US 2019/0170747 A1 Jun. 6, 2019

(30) Foreign Application Priority Data
Mar. 14, 2017 (CN) .......... 2017 1 0149621

(51) Int. Cl.
| | |
|---|---|
| *G01N 33/554* | (2006.01) |
| *G01N 33/569* | (2006.01) |
| *C07K 14/29* | (2006.01) |
| *G01N 33/561* | (2006.01) |
| *G01N 33/68* | (2006.01) |

(52) U.S. Cl.
CPC ........ *G01N 33/56911* (2013.01); *C07K 14/29* (2013.01); *G01N 33/561* (2013.01); *G01N 33/56966* (2013.01); *G01N 33/68* (2013.01); *G01N 2333/195* (2013.01); *G01N 2333/29* (2013.01); *G01N 2333/43552* (2013.01); *G01N 2333/43556* (2013.01)

(58) Field of Classification Search
None
See application file for complete search history.

(56) References Cited

U.S. PATENT DOCUMENTS

2011/0143377 A1   6/2011   Hoey et al.

FOREIGN PATENT DOCUMENTS

WO   2015116907 A1   8/2015

OTHER PUBLICATIONS

Dunning Hotopp et al "Comparative genomics of emerging human ehrlichiosis agents." PLoS Genet. 2:208-222(2006).*
Barbet et al (Genbank Accession No. S5PMH8 Jul. 2013).*
Daugherty et al (Genbank Accession No. A0A0F3PJJ9. Jan. 2015).*
Felsheim et al Genbank Accession No. S6G8R5 Mar. 2013).*

* cited by examiner

*Primary Examiner* — Jennifer E Graser
(74) *Attorney, Agent, or Firm* — SZDC Law PC

(57) ABSTRACT

The present invention relates to use of an Anaplasma phagocytophilum protein APH1384 as diagnostic antigen for granulocytic anaplasmosis. The protein can remedy the drawback of missed detection of an existing diagnostic antigen P44 for granulocytic anaplasmosis, improve sensitivity of detection for granulocytic anaplasmosis, and facilitate rapid and accurate clinical diagnosis of granulocytic anaplasmosis.

2 Claims, 3 Drawing Sheets
Specification includes a Sequence Listing.

APPLICATION OF ANAPLASMA PHAGOCYTOPHILUM PROTEIN APH1384

This application is a National Stage Application of PCT/CN2017/087912, filed on Jun. 12, 2017, which claims priority to Chinese Patent Application No.: 201710149621.X, filed on Mar. 14, 2017, which is incorporated by reference for all purposes as if fully set forth herein.

FIELD OF THE INVENTION

The present invention relates to the field of immunology, and more particularly to use of an anaplasma phagocytophilum protein APH1384.

DESCRIPTION OF THE RELATED ART

Anaplasma phagocytophilum is a tick-borne obligate intracellular gram-negative bacteria that causes granulocytic anaplasmosis, such as human granulocytic anaplasmosis and canine granulocytic anaplasmosis. CDC data showed that in the United States, cases of infection with human granulocytic anaplasmosis increased from 348 cases to 2389 cases from 2000 to 2012, presenting a rapidly increasing trend. In addition, granulocytic anaplasmosis is locally endemic in human populations and domestic animals in Australia, many European countries, Japan and Korea. In China, a seroepidemiological survey from Chinese Center For Disease Control And Prevention indicates that seroprevalence of granulocytic anaplasmosis in farmers is up to 13.9%. Compared to European and American patients with granulocytic anaplasmosis, the conditions of Chinese patients with anaplasmosis are more severe, with a mortality of up to 8.1%. The patients in China may develop other severe symptoms. For example, 41.2% of them may develop multiple organ failure. Also, from the survey by the same institute, seroprevalences against Anaplasma phagocytophilum are up to 10.05% and 3.82% respectively in dogs and sheep. At present, granulocytic anaplasmosis has reached epidemic levels worldwide, and has become a major public health problem. Therefore, improving optimization of diagnostic methods for granulocytic anaplasmosis has a very important and practical significance in medicine, public health, and animal husbandry fields.

Currently, serological diagnosis for granulocytic anaplasmosis uses Anaplasma phagocytophilum antigens to detect specific antibodies against this pathogen in the serum of an infected object, thereby determining whether the subject is infected with anaplasma phagocytophilum. The serological diagnosis mainly includes indirect fluorescent antibody assays (IFA), Western Blotting and Dot Blotting (WB and DB), and ELISA. The ELISA and DB methods are primarily used for detecting a high volume of serum samples from human or animals.

The IFA method uses cells infected with Anaplasma phagocytophilum to prepare antigen slides for detecting specific antibodies against Anaplasma phagocytophilum in clinical serum specimens. By incubating with a secondary antibody labeled with fluorescein, fluorescence intensity on the antigen slides is observed under a fluorescent microscope to determine whether the serum is positive. This technique is the gold standard for clinically detecting infection of granulocytic anaplasmosis currently; however, the operation is complex, the interpretation of results is subjective, and the cost of antigen slides is expensive, so that it is not suitable for clinically detecting a high volume of serum samples. For the WB, DB and ELISA methods, a recombinant protein or protein antigenic epitope polypeptide specific to Anaplasma phagocytophilum is used as diagnostic antigens to detect whether specific antibodies against Anaplasma phagocytophilum are present in serum samples from human or animals. Of them, the ELISA method is simple, can be automatized, and can be used for detecting a high volume of clinical samples. However, these three serological detection methods all use an outer membrane protein P44 of Anaplasma phagocytophilum as diagnostic antigen, and the detection with P44 as a single diagnostic antigen suffers from a disadvantage of missed detection, with a sensitivity of detection of 80-90%. In conclusion, the IFA method has high cost of detection and requires expensive antigen slides with subjective determination results and relatively long operation time, and is not suitable for detecting a high volume of clinical samples; in contrast, the WB, DB and ELISA methods are simple and have low costs, but all use P44 as a single diagnostic antigen currently, so that the disadvantage of missed detection occurs and the sensitivity of detection is to be improved.

SUMMARY OF THE INVENTION

In order to overcome the disadvantages of the above detection methods, an object of the present invention is to provide use of an Anaplasma phagocytophilum protein APH1384. The protein is strongly antigenic, and can remedy the drawback of missed detection of P44 and improve sensitivity of detection for granulocytic anaplasmosis, thereby facilitating rapid and accurate clinical diagnosis of granulocytic anaplasmosis.

The present invention provides use of an Anaplasma phagocytophilum protein APH1384 as diagnostic antigen for granulocytic anaplasmosis.

Preferably, the Anaplasma phagocytophilum protein APH1384 has an amino acid sequence shown in SEQ ID NO: 1.

Preferably, an antigenic epitope of the Anaplasma phagocytophilum protein APH1384 has an amino acid sequence shown in SEQ ID NO: 2.

By means of the foregoing technical solution, the present invention has the following advantages:

The present invention provides a serological diagnostic antigen APH1384 for granulocytic anaplasmosis. The protein can remedy the drawback of missed detection of an existing diagnostic antigen P44 for granulocytic anaplasmosis, improve sensitivity of detection for granulocytic anaplasmosis, and facilitate rapid and accurate clinical diagnosis of granulocytic anaplasmosis.

DETAILED DESCRIPTION OF THE PREFERRED EMBODIMENTS

Figure 1:
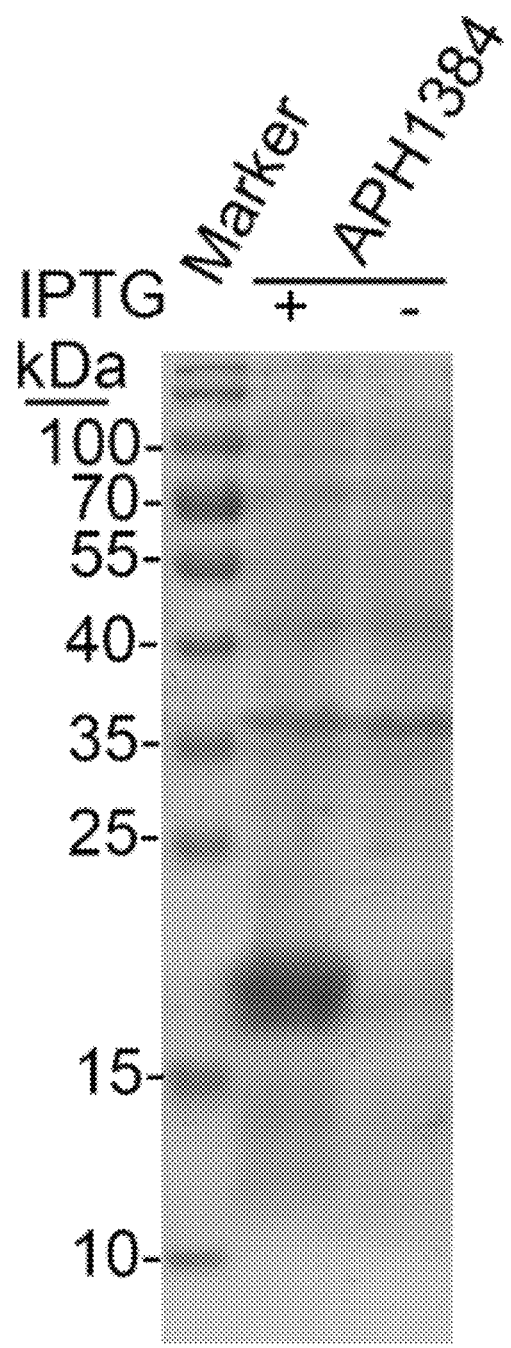
FIG. 1 shows expression result of recombinant APH1384 protein by SDS-PAGE electrophoresis.
Figure 2:
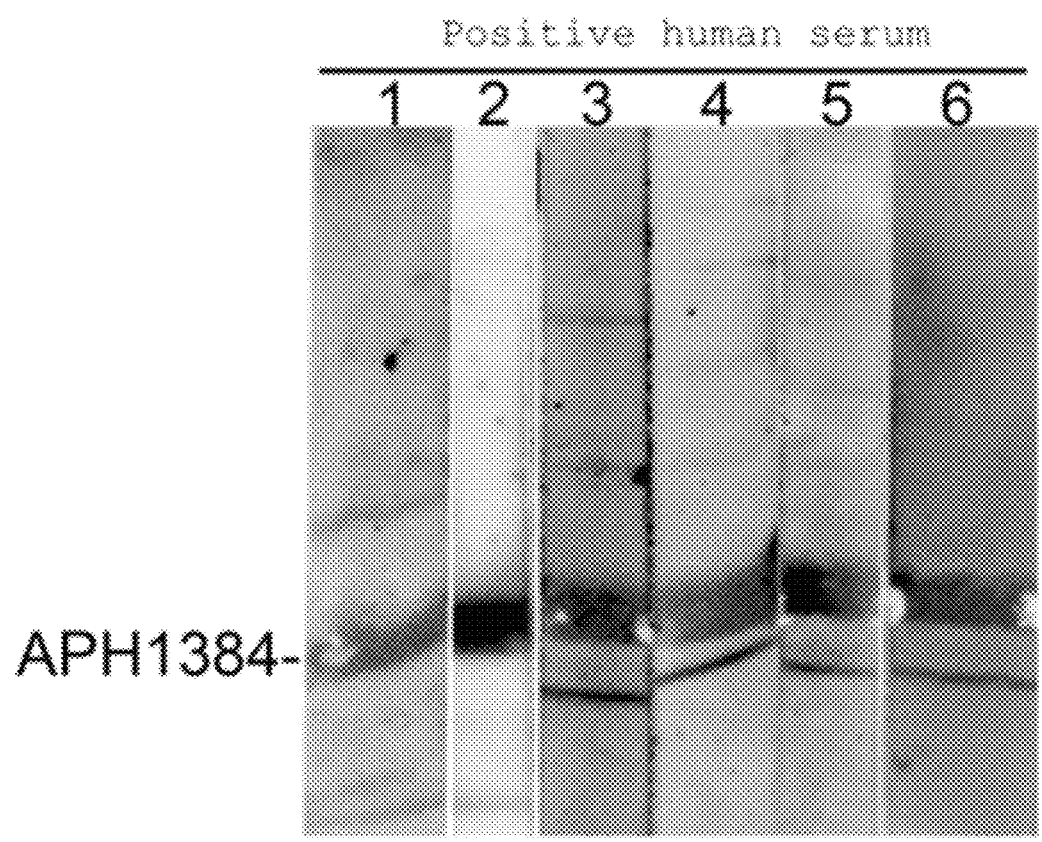
FIG. 2 shows detection results for APH1384 antigenicity by WB technique.
Figure 3:
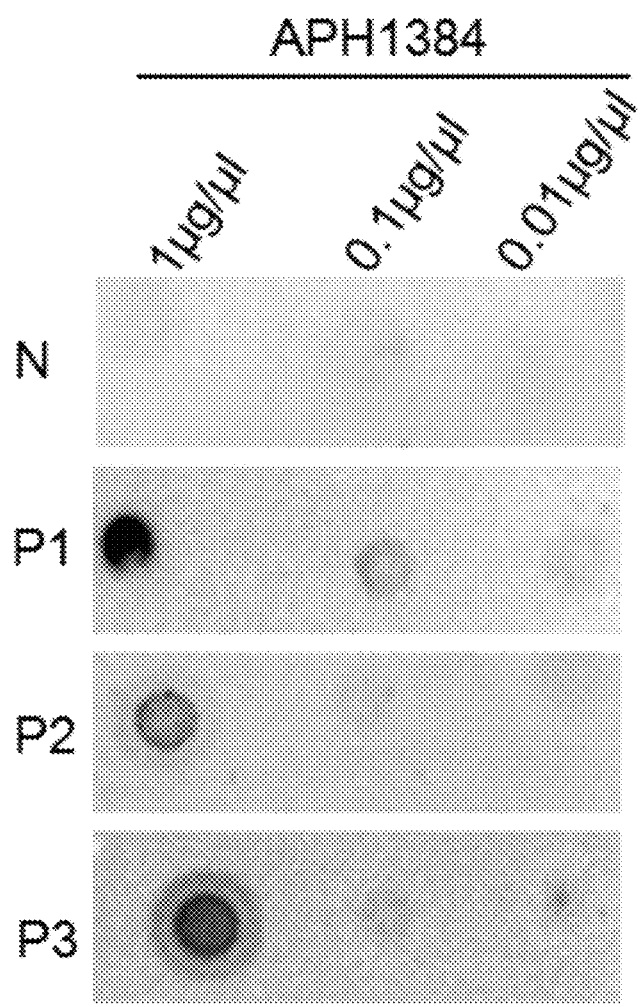
FIG. 3 shows detection results for APH1384 polypeptide antigenicity by DB technique.

The invention will be further illustrated in more detail with reference to the accompanying drawings and embodiments. It is noted that, the following embodiments only are intended for purposes of illustration, but are not intended to limit the scope of the present invention.

Embodiment 1

Preparation of APH1384 protein (a species-specific protein derived from Anaplasma phagocytophilum)

Species-specific proteins derived from Anaplasma phagocytophilum were screened by bioinformatics techniques using 610 proteins of unknown function encoded by the genome of Anaplasma phagocytophilum as targets. Some of the proteins (including APH1384) were subjected to cloning and expression, and antigenic identification. It was found from the research results that APH1384 had strong antigenicity. Detailed steps of cloning and expression, and antigenic characterization of APH1384 were provided as below. Specific primers containing restriction endonuclease sites were designed according to a gene sequence aph1384 in GenBank: aph1384-F-TCCGAATTCATGTTTGATATATTTAATGATGCTG; and aph1384-R-GCACTCGAGTTATTCGGACGCAGAGGCT. A DNA fragment of the gene aph1384 was amplificated by PCR using whole genomic DNA of Anaplasma phagocytophilum as a template. The amplificated target gene DNA fragment and a prokaryotic expression vector pET28a(+) were double-digested by restriction endonucleases, and ligated with T4 DNA ligase. The ligation product was transformed into a cloning host strain *E. coli* TOP10, plasmid was extracted for sequencing, and the recombinant plasmid was transformed into an expression host strain *E. coli* BL21 (DE3) for protein expression. The *E. coli* BL21 (DE3) containing the recombinant plasmid was cultured at 37° C., IPTG was added to induce expression of the APH1384 protein, a pellet was collected by centrifugation after induction for 3.5 h, and the pellet was subjected to denaturation and lysis, and then the expression level of the APH1384 protein was determined by SDS-PAGE electrophoresis. The results are shown in FIG. 1. FIG. 1 shows that a target protein band appears at 21.5 kDa, and no target protein band is present for a control group without addition of IPTG. The APH1384 protein was purified by nickel column affinity chromatography, and amino acid sequence of the APH1384 protein is shown in SEQ ID NO: 1.

The antigenicity of APH1384 was detected by WB technique using 6 Anaplasma phagocytophilum positive sera with the purified recombinant protein APH1384 of Anaplasma phagocytophilum as antigen. Firstly, the purified recombinant APH1384 protein was loaded onto a SDA-PAGE gel, the protein was transferred to a nitrocellulose membrane, and the membrane was cut into strips, blocked for 30 min, incubated with primary positive sera (1:2000), washed 3 times with PBS, incubated with a secondary antibody (HRP labeled goat anti-human IgG, 1:5000), washed 4 times with PBS, and developed. The results are shown in FIG. 2, wherein 1-6 represent the Anaplasma phagocytophilum positive sera respectively, and APH1384 is the species-specific protein derived from Anaplasma phagocytophilum. The results show that 6 positive sera can all react with APH1384. The APH1384 protein presents a strong positive reaction with the Anaplasma phagocytophilum positive sera, and this indicates that APH1384 has strong antigenicity.

Embodiment 2

Preparation of APH1384 Polypeptide

An antigenic epitope of APH1384 was predicted and obtained by bioinformatics methods, and amino acid sequence of the antigenic epitope is shown in SEQ ID NO: 2. An APH1384 antigenic epitope polypeptide was chemically synthesized, and antigenicity of the APH1384 polypeptide was verified by DB technique. Specific operations were provided as below.

Dilutions of the APH1384 polypeptide antigen (1 μl at concentrations of 1 μg/μl, 0.1 μg/μl, and 0.01 μg/μl respectively) were added to a nitrocellulose membrane respectively, and the membrane was dried for 20-30 min at 37° C., blocked for 30 min, incubated with primary human positive sera (1:2000) for 1 h, incubated with a secondary antibody (1:5000) for 1 h, and developed. The results are shown in FIG. 3, wherein N represents a negative serum, and P1-P3 each represents one Anaplasma phagocytophilum positive serum. The results show that the negative serum does not react with APH1384, and three positive sera all are bound to the APH1384 polypeptide, and this indicates that the APH1384 polypeptide has antigenicity.

Embodiment 3

Use of APH1384 Polypeptide

Specific anti-APH1384 antibodies in human sera were detected by ELISA with the synthesized APH1384 polypeptide as coating antigen. Specific operation steps were provided as below:

(1) coating: the APH1384 polypeptide synthesized in example 2 was diluted to 20 μg/ml with PBS, and coated onto a plate overnight at 4° C. or for 2 h at room temperature (96-well plate, 50 μl/well);

(2) blocking: the 96-well plate was washed 3 times with PBS, and a blocking solution of bovine serum albumin (at a concentration of 1% (w/v)) was added in 200 μl/well at 37° C. for 2 h;

(3) incubation with a primary antibody: the serum to be detected was diluted at a ratio of 1:1000 using the blocking solution, and the dilution was added in 100 μl/well and incubated for 1 h at 37° C.;

(4) incubation with a secondary antibody: the 96-well plate was washed 4 times with PBS (200 μl/well), and the secondary antibody (HRP labeled goat anti-human IgG, 1:5000 dilution) was added and incubated for 1 h at 37° C.; and (5) developing: the 96-well plate was washed 3-5 times with PBS, a prepared developing solution was added in 100 μl/well, and immediately after in the dark at 37° C. for 10-15 min, a stopping solution (1 M hydrochloric acid) was added in 100 μl/well to stop the reaction. Within 15 min after the reaction was stopped, absorbance of the solution in each well was determined at a wavelength of 450 nm; and (6) determination of results: a Cutoff value was calculated (Cutoff value=average of negative controls+3*SD), and then the absorbance in the detected well was compared with the Cutoff value. The absorbance in the detected well being higher than the Cutoff value indicates that the antibody against Anaplasma phagocytophilum in the serum is positive; and the absorbance in the detected well being lower than the Cutoff value indicates that the antibody against Anaplasma phagocytophilum in the serum is negative.

Embodiment 4

Use of APH1384 Polypeptide

Specific anti-APH1384 antibodies in human sera were detected by DB with the synthesized APH1384 polypeptide as an antigen. Specific operation steps were provided as below:

(1) spotting: the APH1384 polypeptide antigen was diluted with PBS (0.01 M, pH 7.4) to suitable concentrations (1 μg/μl, 0.1 μg/μl, 0.01 μg/μl respectively), and 1 μl of the dilution was added to a nitrocellulose membrane with a pipetter, and the membrane was placed and dried in an incubator at 37° C. for 20-30 min;

(2) blocking: 5 ml of a blocking solution (5% skimmed milk powder) was added into the incubator, and blocking is performed for 30 min at room temperature;

(3) incubation with a primary antibody: the blocking solution was discarded, and the human serum specimen diluted with the blocking solution (1:2000) was added, incubated for 1 h at room temperature, and washed 3 times with PBS for 10 min each;

(4) incubation with a secondary antibody: the HRP-goat anti-human IgG secondary antibody diluted with the blocking solution (1:5000) was added, incubated for 1 h at room temperature, and washed 3 times with PBS for 10 min each; and (5) developing: developing of the spot at 1 μg/μl was observed by the ECL chemiluminescence, so as to determine whether the antibody against Anaplasma phagocytophilum in the serum is negative or positive. The negative control serum shows no developed spot on the membrane. The presence of a visual spot indicates that an antibody against Anaplasma phagocytophilum in the serum is positive; and the absence of a visual spot indicates that an antibody against Anaplasma phagocytophilum in the serum is negative.

The APH1384 protein or the synthesized polypeptide antigen of the present invention serves as diagnostic antigen for granulocytic anaplasmosis, and a specific antibody in a multi-species serum can be detected by multiple serological methods to diagnose whether the species is infected with Anaplasma phagocytophilum. The serological methods include, but are not limited to ELISA, DB and WB, and the multi-species serum includes that from a human, a dog, a cat, or a horse and so on.

The above description is only preferred embodiments of the present invention and not intended to limit the present invention, it should be noted that those of ordinary skill in the art can further make various modifications and variations without departing from the technical principles of the present invention, and these modifications and variations also should be considered to be within the scope of protection of the present invention.

What is claimed is:

1. A method for diagnosing granulocytic anaplasmosis in a subject comprising:
   providing an APH1384 antigenic epitope polypeptide having an amino acid sequence shown in SEQ ID NO: 2; and
   detecting anti-APH1384 antibodies in the subject using the APH1384 antigenic epitope polypeptide as an antigen,
   wherein the anti-APH1384 antibodies are the antibodies of an *Anaplasma phagocytophilum* protein APH1384 in the subject.

2. The method as claimed in claim 1, wherein the *Anaplasma phagocytophilum* protein APH1384 has an amino acid sequence shown in SEQ ID NO: 1.

* * * * *

SEQUENCE LISTING

<160> NUMBER OF SEQ ID NOS: 2

<210> SEQ ID NO 1
<211> LENGTH: 160
<212> TYPE: PRT
<213> ORGANISM: ANAPLASMA PHAGOCYTOPHILUM
<220> FEATURE:
<223> OTHER INFORMATION: Amino Acid Sequence of the APH1384 Protein

<400> SEQUENCE: 1

```
Met Phe Asp Ile Phe Asn Asp Ala Val Val Ala Ser Val Ser Thr
1               5                   10                  15

Ala Pro Thr Gly Thr His Leu Ser Phe Pro Gly Ala Cys Gly Asp
                20                  25                  30

Phe Ser Leu Glu Asn Leu Pro Leu Ile Lys Ser His Ser Phe Glu
                35                  40                  45

Tyr Asp Leu Val Thr Gly Tyr Glu Tyr Thr Val Leu Arg Phe Gly
                50                  55                  60

Ser Glu Lys Gln Glu Asp Gln Asn Ser Ser Thr Tyr Met Leu Asp
                65                  70                  75

Val Phe Phe Arg Arg Val Pro Asp Ser Asn Asp Ile Ser Leu Tyr
                80                  85                  90

Ser Val Glu Trp Gly Glu Val Leu Ser Asn Ala Asn Thr Val His
                95                  100                 105

Glu Lys Gln Ser Glu Asp Leu Arg Glu Lys Gly Arg Ser Met Ala
                110                 115                 120

Met Cys Gly Leu Met Pro Asp Ser Thr Val Glu Gln Asp Gly Ala
                125                 130                 135

Leu Val Leu Thr Ser Thr Gly His Ala Ala Lys Cys Lys Val Thr
                140                 145                 150

Val Thr Leu Lys Val Ala Ser Ala Ser Glu
                155                 160
```

<210> SEQ ID NO 2
<211> LENGTH: 29
<212> TYPE: PRT
<213> ORGANISM: Artificial sequence
<220> FEATURE:
<223> OTHER INFORMATION: Amino Acid Sequence of the Antigenic Epitope -continued

```
<400> SEQUENCE: 2

Phe Gly Ser Glu Lys Gln Glu Asp Gln Asn Ser Ser Thr Tyr Met
1               5                   10                  15

Leu Asp Val Phe Phe Arg Arg Val Pro Asp Ser Asn Asp Ile
                20                  25
```